United States Patent

Wren

[11] 4,418,206
[45] Nov. 29, 1983

[54] 9-DEOXY-9-METHYLENE DERIVATIVES OF (DL)-16-PHENOXY AND 16-PHENOXY SUBSTITUTED PROSTATRIENE COMPOUNDS

[75] Inventor: Douglas L. Wren, Palo Alto, Calif.

[73] Assignee: Syntex (U.S.A.) Inc., Palo Alto, Calif.

[21] Appl. No.: 360,286

[22] Filed: Mar. 22, 1982

[51] Int. Cl.$^3$ .......................................... C07C 177/00
[52] U.S. Cl. ........................................ 560/55; 560/61;
560/62; 562/465; 562/471; 562/472; 568/435;
568/442; 568/630; 568/656; 424/308; 424/317;
424/333; 424/340; 260/501.1; 260/501.13
[58] Field of Search ............................ 560/55, 61, 62;
562/465, 471, 472; 568/435, 442, 630, 656;
424/308, 317, 333, 340; 260/501.1, 501.13

[56] References Cited

PUBLICATIONS

Derwent Abstract 81074x/43, U.S. Pat. No. 3,985,791, 23.06.75.
Derwent Abstract 92730b/51, U.S. Pat. No. 4,178,457, 10.07.78.
Derwent Abstract 81996a/45, U.S. Pat. No. 4,123,463, 21.03.78.
Derwent Abstract 20192c/11, U.S. Pat. No. 4,191,837, 05.04.78.

Primary Examiner—Paul J. Killos
Attorney, Agent, or Firm—James M. Kanagy; Tom M. Moran

[57] ABSTRACT

Novel compounds of the formula:

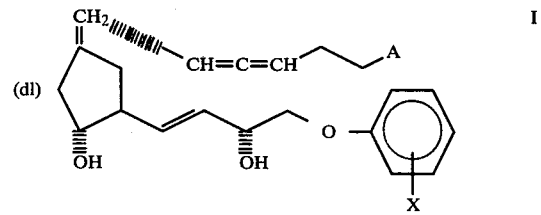

wherein A is CHOH, CHO or COOR; R is hydrogen or a lower alkyl group of 1 to 4 carbon atoms; and the pharmaceutically acceptable, non-toxic salts of compounds in which R is hydrogen; and X is hydrogen, o-, m- or p-halo(fluoro, chloro or bromo), o-, m- or p-methyl or o-, m- or p-methoxy. These compounds possess prostaglandin-like activity and thus are useful in the treatment of mammals where prostaglandins are indicated. They are particularly useful as inhibitors of gastric acid secretions and as agents for the control of asthmatic attack, because of their bronchodilating activity.

19 Claims, No Drawings

9-DEOXY-9-METHYLENE DERIVATIVES OF (DL)-16-PHENOXY AND 16-PHENOXY SUBSTITUTED PROSTATRIENE COMPOUNDS

BACKGROUND OF THE INVENTION

1. Description of the Invention

The present invention relates to certain novel 9-deoxy-9-methylene prostaglandins. More particularly, the present invention relates to 9-deoxy-9-methylene substituted derivatives of (dl)-11α,15α-dihydroxy-16-phenoxy-17,18,19,20-tetranorprosta-4,5,13-(trans)-triene alcohols, aldehydes, and acids as well as the pharmaceutically acceptable, non-toxic lower alkyl esters and salts of the acid and the processes for preparing such compounds.

2. Related Art

Prostaglandin have classically been described as chemically related 20 carbon acid hydroxy fatty acids having the basic skeleton of prostanoic acids:

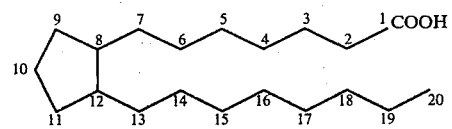

The prostaglandins having a hydroxyl group at the C-11 and a keto group at the C-9 position are known as the PGE series, those having an hydroxyl group in place of the keto group are known as the PGF series and are further designated by an α or β suffix to indicate the configuration of the hydroxyl group at the said position. The natural compounds are the α-hydroxy substituted compounds. They may contain different degrees of unsaturation in the molecule, particularly at C-5, C-13 and C-17, the unsaturation is also indicated by a suffix. Thus, for example, the $PGF_1$ and $PGE_1$ series refer to prostanoic acid having a trans olefin bond at the C-13 position, while the $PGF_2$ and $PGE_2$ series refer to prostadienoic acids having a cis-olefin bond at the C-5 position and a trans olefin bond at the C-13 position. For a review on prostaglandins and the definition of primary prostaglandins, see for example, S. Bergstrom, *Recent Progress in Hormone Research* 22, pp. 153–175 (1966) and Science 157, p. 382 (1967) by the same author.

The preparation of derivatives of prostanoic acid has been extensive. The great majority of these studies have focused on modification of the two side chains, or modification of the substituents attached to the cyclopentane moiety. The synthesis of prostaglandin analogs having diethylenic (allenic) unsaturation in the carboxylic acid chain has been described in U.S. Pat. No. 3,879,438 issued to Crabbe and Fried. The synthesis of several prostaglandin analogs in which the alkyl chain attached to C-15 in the natural compound is replaced by an aryloxymethylene group has been reported in, for example, the U.S. Pat. Nos. 3,864,387, 3,954,881 and Belgium Pat. No. 806,995. Prostaglandins having 4,5-allenic unsaturation and 16-phenoxy and substituted 16-phenoxy-9-keto compounds are reported in U.S. Pat. No. 4,178,457 issued to Van Horn et al. Prostanoic acid derivatives having 9-deoxy-9-methylene-(trans)-2,3-didehydro-$PGF_1$ are disclosed in U.S. Pat. No. 4,165,436. See also U.S. Pat. No. 4,296,256 which relates to 2-decarboxy-2-hydroxymethyl-19-keto-PG compounds.

SUMMARY OF THE INVENTION

In accordance with the present invention we have prepared certain novel 9-deoxy-9-methylene-16-phenoxy- and substituted 16-phenoxy prostaglandin analogs represented by the following formula:

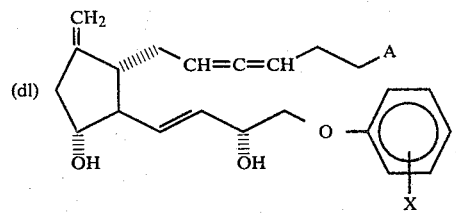

wherein A is CHOH, CHO, or COOR; R is hydrogen or a lower alkyl group of 1 to 4 carbon atoms, or the pharmaceutically acceptable, non-toxic salts of compounds in which R is hydrogen; and X is hydrogen, o-, m- or p-halo (fluoro, chloro or bromo), o-, m- or p-methyl or o-, m- or p-methoxy.

The compounds of the present invention exhibit prostaglandin-like biological activities and are thus useful in the treatment of mammals where the use of prostaglandins is indicated. The compounds of Formula I are extremely usefuly in the treatment and prevention of gastric and duodenal ulcers.

In another instance this invention relates to a pharmaceutical composition comprising one or more compounds of Formula I in admixture with a pharmaceutically acceptable excipient.

In yet another instance this invention relates to a process for preparing compounds of formula 1 which process comprises:

(a) reducing a compound of Formula I wherein A is COOR and R is hydrogen to a compound of Formula I wherein A is CHOH; or (b) oxidizing a compound of Formula I wherein A is CHOH to a compound of Formula I wherein A is CHO; or (c) converting a compound of Formula I wherein A is COOR and R is a lower alkyl group of 1 to 4 carbon atoms to a compound of Formula I wherein A is COOR and R is hydrogen by hydrolysis; or (d) converting a compound of Formula I wherein A is COOR and R is hydrogen to a compound of Formula I wherein R is a pharmaceutically acceptable, non-toxic salt.

DESCRIPTION AND PREFERRED EMBODIMENTS

Various terms and structural representations used herein should be understood to read according to the following annotations unless otherwise specified.

The line shown in the above formula and in the formulas below as

indicate that the substituents are in the α configuration, i.e., below the plane of the cyclopentane ring.

The double bond at C-13 and the compounds of the present invention have the same configuration in natural prostaglandins of the PGE and PGF series, that is the trans configuration.

These novel compounds possess asymmetric centers and thus can be produced as racemic "(dl)" mixtures or as individual enantiomers. The racemic mixtures can be resolved if desired at appropriate stages by methods known to those skilled in the art, to obtain their respective individual enantiomers.

The term "lower alkyl" as used herein, unless otherwise specified, refers to a straight or branched alkyl group containing up to four carbon atoms, e.g., methyl, ethyl, n-propyl, isopropyl, n-butyl, and the like.

The term "pharmaceutically acceptable, non-toxic salts" refers to the salts prepared from pharmaceutically acceptable non-toxic bases, including inorganic bases and organic bases. Salts derived from inorganic bases include sodium, potassium, lithium, ammonium, calcium, ferrous, ferric, aluminum, zinc, cuprous, cupric, manganous, manganic salts and the like. Particularly preferred are the ammonium, potassium, sodium, calcium and magnesium salts. Salts derived from pharmaceutically acceptable organic non-toxic bases include salts of primary, secondary and tertiary amines. Substituted amines include naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucose amine, N-methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline, and caffeine.

The compounds in the present invention exhibit prostaglandin-like biological activity and thus are used in the treatment of mammals where the use of prostaglandins are indicated. The compounds of the present invention are useful for the control of asthmatic attacks because they are bronchodilators and they also exhibit antiallergic properties by inhibition of mediator release. In addition, they are also useful in treating mammals for bronchial spasms or wherever bronchodilators are indicated. The compounds also exhibit vasodilator properties and are useful in controlling or palliating hypertension in mammals. They further exhibit central nervous system depressant activity in mammals, and are useful as sedatives.

More particularly, these 9-deoxy-9-methylene-16-phenoxy-4,5,13-prostatriene compounds of Formula I are potent inhibitors of gastric secretion and ulcer induction. Thus, the compounds of Formula I are extremely useful in the treatment and prevention of gastric and duodenal ulcers.

The present compounds can be administered in a wide variety of dosage forms, either alone or in combination with other pharmaceutically compatible medicaments, in the form of pharmaceutical compositions suited for oral or parenteral administration or inhalation in the case of bronchodilators. They are typically administered as pharmaceutical compositions consisting essentially of the free acid, salt, ester, aldehyde or alcohol and a pharmaceutical carrier. The pharmaceutical carrier can be either a solid material, liquid or aerosol, in which the compound is dissolved, dispersed or suspended, and can optionally contain small amounts of preservative and/or pH buffering agents. Suitable preservatives which can be used include, for example, benzyl alcohol and the like. Suitable buffering agents include, for example, sodium acetate and pharmaceutical phosphate salts and the like.

The liquid compositions can, for example be in the form of solutions, emulsions, suspensions, syrups, or elixirs. The solid compositions can take the form of tablets, powders, capsules, pills or the like, preferably in unit dose form for simple administration or precise dosages. Solvents which may be used for preparing stable solutions of the subject compounds are, for example, ethanol, low molecular weight PEGs, dimethyl PEGs, triacetin, citrate triacetate, propylene carbonate and the like. Suitable solid carriers include, for example, pharmaceutical grades of starch, lactose, sodium saccharine, talcum, sodium bisulfite, povidone and the like.

For inhalation administration, free acids, salts, esters, adlehydes or alcohols can be administered as an aerosol comprising the compound in an inert propellant together with a cosolvent, e.g., methanol, together with optional preservatives and buffering agents. Additional general information concerning inhalation administration of aerosols can be had by reference to U.S. Pat. Nos. 2,868,691 and 3,905,355.

The compounds of this invention are typically administered in dosages of about from 0.01 microgram to about 100 microgram per Kg of body weight. The precise effective dose will, of course, vary depending upon the mode of administration, condition being treated and subject. Thus, for example, to achieve bronchodilation about 1 microgram to about 10 microgram per Kg of body weight is administered by aerosol. To achieve inhibition of gastric secretions about 1 microgram to about 50 microgram per Kg of body weight is administered orally.

The novel 9-deoxy-9-methylene compounds of the present invention can be obtained by a process illustrated by the following sequence of reactions wherein X has the above-indicated meanings; and R is a lower alkyl group of 1 to 4 carbon atoms, but preferably methyl. The presence of t-butyldimethylsilyloxy substituents is herein abbreviated to TDS.

REACTION SCHEME

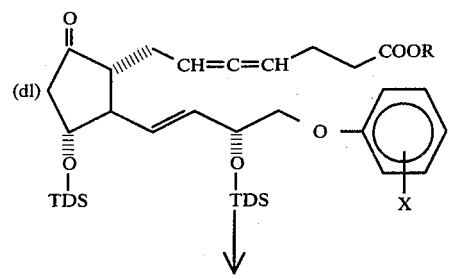

(1)

-continued REACTION SCHEME

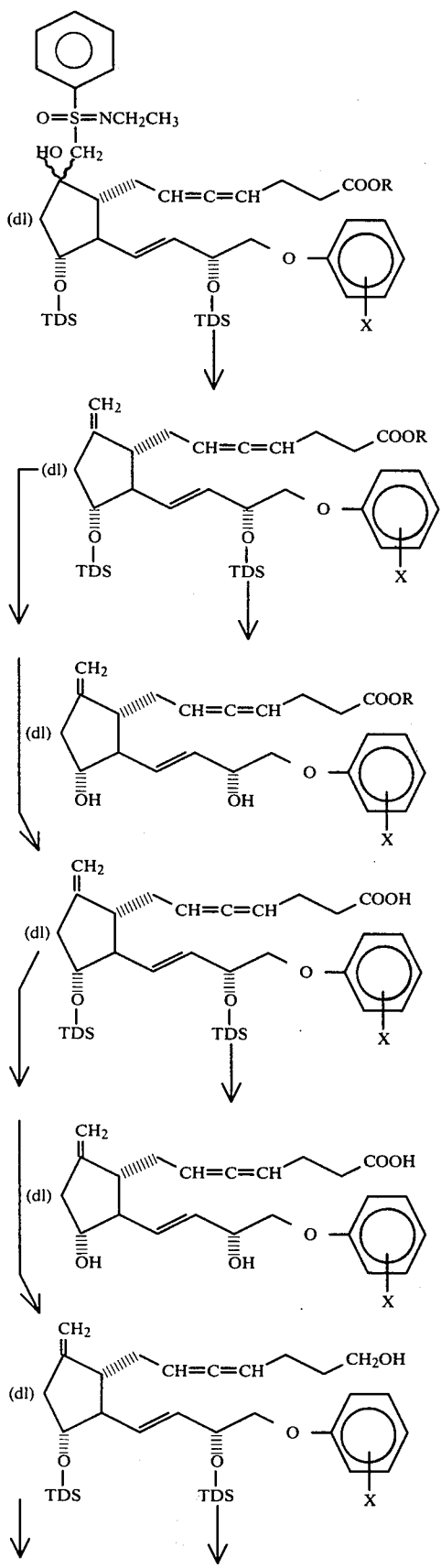

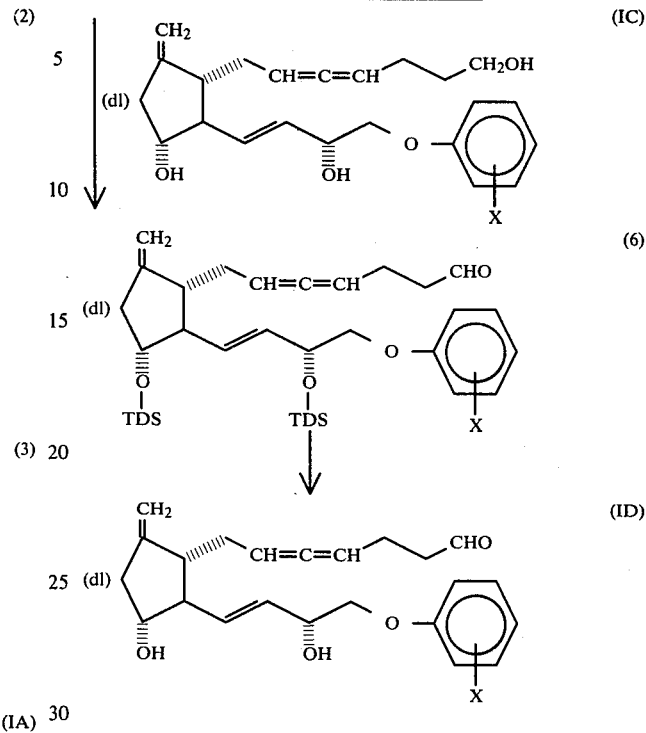

The Formula (1) starting material is prepared according to the procedures set forth in U.S. Pat. No. 3,985,791, which procedures are incorporated herein by reference and made a part hereof.

The transformation of Formula (1) ketones to the corresponding methylene compounds of Formula (2) proceeds by methods known in the art. Particularly useful is the procedure disclosed by Kimball et al, Prostaglandins, Vol. 17, pp. 657–666 (1979). This procedure first requires the generation of the carbanion of an N-alkyl derivative of an S-methyl-S-arylsulfoximine, for example, the carbanion of S-methylphenyl-N-ethyl-S-phenyl-sulfoximine from methylphenyl-N-ethyl-sulfoximine. This carbanion can be obtained by the procedure set out in by Johnson, C. R., et al, J. Am. Chem. Soc., 95:6462, (1973). by reacting the corresponding N-alkyl-S-methyl-S-arylsulfoximine wih any of the usual reagents which will extract an active hydrogen from such sulfoximines, for example, an alkyl lithium or alkyl magnesium halide and the like. The Formula (1) compound is then mixed with the carbanion thusly generated and the resulting material mixed with aluminum amalgam in the presence of acetic acid and water to yield the Formula (3) product.

In the above process the use of a slight molar excess of the N-alkyl-S-aryl-S-methylsulfoximine in relation to the Formula (1) compound is preferred. One mole equivalent of the hydrogen extracting reagent; e.g., methyl magnesium chloride or butyl lithium is used for each equivalent of sulfoximine. The reaction of the carbanion with the Formula (1) compound is carried out in the range of about 0° to −100° C., preferably below about −50° C. An inert reaction diluent is employed, preferably one which is adapted for ease of isolation of reaction products and is readily miscible with water. Accordingly, tetrahydrofuran is a suitable reaction diluent for the present purposes.

When the reaction of the Formula (1) compound with the carbanion is complete, the resulting product is isolated by procedures known in the art or alternatively the entire reaction mixture is used in a subsequently required reaction with the aluminum amalgam.

The conversion of Formula (2) compounds to Formula (4) compounds is carried out by contacting the reaction product of Formula (2) compound and said carbanion with aluminum amalgam prepared as per the Kimball reference in the presence of aqueous acetic acid and at a temperature range of about −20° to 50° C. preferably in the range of 0° C. to 25° C. Other carboxylic acids are alternatively employed in place of acetic acid, for example, propionic acid, butyric acid and citric acid. Mineral acids, e.g., hydrochloric acid, are also useful for this purpose. The amounts of aluminum amalgam and acetic acid are not critical; provided that sufficient molecular equivalents of each are used to reduce each molecular equivalent of the carbanion-Formula (2) reaction product. The use of a large excess of aluminum amalgam and acid is preferred. The amount of water present in the reaction mixture is not critical, provided, however, that sufficient water is present to provide an ionizing reaction system. Also, a sufficient quantity of water-miscible inert organic diluent is employed to provide a mobile and substantially homogeneous reaction mixture.

Treatment of the carbanion-Formula (2) reaction product with the aluminum amalgam-acetic acid solution can additionally effect the hydrolysis of the silyl groups at C-11 and C-15 depending on the temperature used and length of reaction time. If the reaction is carried out at about 0°-35° C. for several hours, for example, 0.5 to 5 hours, a compound of Formula (3) is obtained. For this product, Formula (3), it is preferred to carry out the reaction at room temperature for 2-4 hours. If the trienoic acid methyl ester is required, Formula (IA), that can be achieved by maintaining the carbanion-Formula (2) mixture at a higher temperature than noted above and extending the reaction time. For example hydroylsis of the silyl groups may be realized by maintaining the reaction temperature between about 30°-70° C. for a period between about 6 and 24 hours. To achieve this hydrolysis via these reagents, it is preferred to maintain the solution, with stirring, at about 50° C. for about 12 hours.

In the event the above reaction conditions do not completely hydrolyze all silyl esters or an hydrolysis of these protecting groups is otherwise desired, hydrolysis of the silyl protecting groups can be carried out treating the protected compound in an inert polar organic solvent with a small amount of a strong mineral acid such as hydrogen fluoride or HCl or an organic acids such as formic acid, acetic or the like etc. This reaction may be carried out at between about 0°-50° C. for a period of 0.25 to 6 hours. Usually the reaction will be carried out in acetonitrile, diethyl ether, tetrahydrofuran and the like, preferably acetonitrile, at room temperature for 1 hour. Such a procedure is effective for removing the silyl esters of Formulas (3), (4), (5) or (6).

The further hydrolysis of Formula (3) or (IA) compounds to obtain the free acid compounds of Formula (4) or (IB) respectively is carried out biologically or with a dilute solution of a strong inorganic base. Biological hydrolysis proceeds by an enzymatic process preferably using pancreatic lipase preparations to cleave the ester (preferably the methyl ester) group, thus yielding the free acid. Alternatively, the alkyl ester may be cleaved by employing a dilute solution of a strong inorganic base in an aprotic water-miscible organic solvent. This reaction is preferably carried out with a dilute aqueous solution of an alkyli metal hydroxide such as lithium hydroxide, potassium hydroxide, sodium hydroxide, or the like, in conjunction with an aprotic water-miscible inert solvent. There may be used, for example, a 0.25 to 2 molar aqueous solution of lithium hydroxide with an organic solvent such as tetrahydrofuran, diethyl ether, diglime, methanol or the like. Preferably a 1 molar solution of lithium hydroxide will be used in equal proportions with tetrahydrofuran. The reaction is carried out at between about 0°-50° C., preferably at ambient temperature for about 1 to 5 hours, preferably 2 to 4 hours.

The salt derivatives of the 9-deoxy-9-methylene prostatrienoic free acids of the present invention can be prepared by treating the corresponding free acids with about 1 molar equivalent of a pharmaceutically acceptable base, including inorganic and organic, bases per molar equivalent of free acid. Particularly preferred inorganic salts are the ammonium, potassium, sodium, calcium and magnesium salts. Particularly preferred organic non-toxic salts are isopropylamine, diethylamine, ethanolamine, piperidine, tromethamine, choline and caffeine.

The reaction is conducted in water alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratios of the free acid to base used is chosen to provide the ratio desired for any particular salt. For preparing, for example, the calcium salts or magnesium salts, the free acid starting material can be treated with at least 0.5 molar equivalent of a pharmaceutically acceptable base to yield a neutral salt. When the aluminum salts are prepared, at least one third molar equivalent of the pharmaceutically acceptable base are employed if a neutral salt is desired.

In the preferred procedure, the calcium salts and magnesium salts of the Formula (IB) prostatrienoic acid compounds hereof can be prepared by treating the corresponding sodium or potassium salts with at least 0.5 molar equivalent calcium chloride or magnesium chloride, respectively, in an aqueous solution, alone or in combination with an inert water-miscible organic solvent, at a temperature of from about 20° C. to about 100° C. Preferably, the aluminum salts of the prostatrienoic acids of the present invention can be prepared by treating the corresponding free acids with at least one third molar equivalent of aluminum alkoxide, such as aluminum triethoxide, aluminum tripropoxide and the like, in a hydrocarbon solvent, such as benzene, xylene, cyclohexane and the like, at a temperature of about 20° C. to about 80° C. Similar procedures can be used to prepare salts of inorganic bases which are not sufficiently soluble for easy reaction. Salt products are isolated by conventional methodologies.

Compounds of Formula (4) can be converted to Formula (5) type compounds, an alcohol, by treating the free acid with a metal hydride reducing agent in a polar aprotic solvent according to methods well known in the art. See for example, Gaylord, N. G., *Reduction with Complex Metal Hydrides*, Wiley-Interscience, New York, pp 322-373, 1956. Any of the several alkali metal hydride complexes, excepting sodium borohydride, may be used for converting the acid to the alcohol. For example there may be used lithium aluminum hydride, sodium aluminum hydride, lithium borohydride, and the like. While a ratio of 0.75 moles of hydride for every 1 mole of acid may be sufficient to effect reduction of the acid to the alcohol, it is preferred to use an excess of the hydride complex for best yields. That excess may be in an amount of about 1 to 1.5 moles of metal hydride for every mole of acid to be reduced. The reaction is carried out under anhydrous conditions in a polar solvent which can act as a Lewis base with regard to the alkali metal hydride. Generally diethyl ether, tetrahydrofuran, 1,2-dimethoxyethane, diglme, or a like solvent is used to carry out the reaction. Reaction temperatures may vary between about 0°–40° C. and the reaction may be carried out over a period of from about 2 to 8 hours. Herein it is preferred to use lithium aluminum hydride in tetrahydrofuran in an amount of 1 mole of the hydride for every mole of acid. The reaction preferably will be carried out at room temperature for a period of about 5 hours.

Excess alkali metal hydride is destroyed prior to isolation of the alcohol. Preferably this will be done with a reagent which will not cause the evolution of hydrogen and which will not interfere with product isolation. There may be used for example a dilute aqueous solution of a water-soluble organic acid such as formic acid, acetic acid, propionic acid or the like. Alternatively, there may be used a organic solution of an acid containing organic solvent solution wherein the organic solvent is reducable by the unreacted metal hydride. Hydrogen fluoride in acetonitrile serves this purpose well and is illustrative of this group of reagents.

Destruction of unreacted metal hydride by either of the two types of reagents is done at a temperature between about 0° C. and 50° C. by adding a moderate molar excess of acid/solvent relative to the theoretical molar excess of metal hydride employed to effect the reaction.

Compounds of Formula (6) are prepared from Formula (5) compounds by selective oxidation of the primary alcohol to the ketone via some strong oxidizing agent under selective conditions which minimizes oxidation to the acid. There may be used for example a chromium trioxide-pyridine complex or the like. Normally the reaction will be carried out under anhydrous conditions under an inert atmosphere in an polar organic solvent which is inert to the oxidizing reagent, such as a halogenated hydrocarbon, at a temperature between about 0°–100° C. for a period of about 1 to 8 hours.

Herein it is preferred to use Collins reagent as described by J. C. Collins, W. W. Hess and F. J. Frank, in Tetrahedron Letters, p 3363 (1968), a chromium trioxide-pyridine complex in a halogenated hydrocarbon solvent system. (molar quantities of reagent and reactant) The reaction is carried out in an anhydrous organic solvent in an inert atmosphere. Preferable organic solvents are, for example, methylene chloride, carbon tetrachloride, ethylene dichloride, pyridine or the like. An inert atmosphere is maintained by the use of an inert gas such as dry nitrogen. About 0.5 to 5 hours is generally sufficient time to effect the reaction. Usually a temperature between 0°–50° C. is sufficient. Preferably the reaction will be carried out in dry pyridine under a nitrogen atmosphere for 1 hour at room temperature.

Isolation of the reaction product is accomplished by decanting the supernatant from the reaction residue, washing the organic layer with several portions of water. The organic layer is then dried over sodium sulfate, for example, and concentrated preparatory to separating the product via chromatography on some suitable chromatographic medium, for example silica gel.

DESCRIPTION OF SPECIFIC EMBODIMENTS

The following Preparations and Examples are given to enable those skilled in the art to more clearly understand and better practice the present invention. They should not be considered limitative of the scope of the invention but merely to be illustrative and representative thereof.

EXAMPLE 1

This example represents a method for converting a compound according to Formula (1) to a 9-deoxymethylene compound of Formula (3) by way of a Formula (2) compound.

To a stirred solution of methylphenyl-N-ethylsulfoximine (330 mg) and 5.2 ml of tetrahydrofuran under a nitrogen atmosphere cooled to 0°–5° C. was added methyl magnesium chloride (0.568 ml of a 3.0 M solution in tetrahydrofuran). After stirring for 20 minutes the resulting mixture is cooled to −78° C. and there is added dropwise a solution of 400 mg of (dl)-9-keto-11α,15α-bis-t-butyldimethylsilyloxy-16-phenoxy-17,18,19,20-tetranorprosta-4,5,13-(trans)-trienoic acid methyl ester, as prepared in U.S. Pat. No. 4,178,457, in 5 ml of THF. Thereafter the resulting mixture was stirred for 2 hours after which a three equivalent excess of sulfoximine was added. After stirring for an additional 1 hour at −78° C., 2.5 ml of saturated ammonium chloride was added, solids removed by filtration and the tetrahydrofuran distilled off. The residue is taken up in 2.5 ml of ethylacetate and washed with water (2×5 ml). After drying the ethyl acetate layer with sodium sulfate, the solvent was evaporated and the residue taken up in 5 ml of tetrahydrofuran. This solution was then treated with aluminum amalgam prepared according to the following procedure:

Aluminum, 3.0 g, was added to 3.0 g of mercuric chloride in 75 ml of water. The resulting mixture was then shaken until evolution of hydrogen gas becomes appreciable (about 20–30 sec). Thereafter the solvent was decanted and the resulting amalgam washed successively with methanol and diethyl ether. This amalgam was then added to a solution of Formula (2) in 5 ml of tetrahydrofuran from above along with 0.2 ml of acetic acid, and 0.2 ml of water. The reaction mixture was then stirred at 15° to 20° C. for two hours and thereafter celite filter aid (2 g) was added. The resulting mixture was then stirred for 5 minutes and filtered through a pad of celite filter aid. The solid residue was then washed with tetrahydrofuran and the combined filtrates concentrated under reduced pressure. The concentrate was dissolved in ethyl acetate (50 ml) and a 10 ml of aqueous saturated monosodium phosphate added. The organic layer was washed with brine and then dried over sodium sulphate. Solvent removal under reduced pressure yielded a residue which was chromatographed on 20 g of silicia gel using first 1% ethyl acetate/methanol (500 ml) followed by 2% ethyl acetate/methanol (500 ml). appropriate eluant fractions were combined and the solvent evaporated to give an oil comprising (dl)-9-deoxy-9-methylene-11α,15α-bis-t-butyldimethylsilyloxy-16-phenoxy-17,18,19,20-tetranorprosta-4,5,13-(trans)-trienoic acid methyl ester.

In like manner other esters corresponding to the Formula (1) can be converted to the corresponding 9-deoxy-9-methylene ester compounds.

(dl)-9-deoxy-9-methylene-11α,15α-bis-t-butyldimethylsilyloxy-16-o-fluorophenoxy-17,18,19,20-tetranorprosta-4,5,13-(trans)-trienoic acid methyl ester, (dl)-9-deoxy-9-methylene-11α,15α-bis-t-butyldimethylsilyloxy-16-m-fluorophenoxy-17,18,19,20-tetranorprosta-4,5,13-(trans)-trienoic acid methyl ester, (dl)-9-deoxy-9-methylene-11α,15α-bis-t-butyldimethylsilyloxy-16-p-fluorophenoxy-17,18,19,20-tetranorprosta-4,5,13-(trans)-trienoic acid methyl ester, (dl)-9-deoxy-9-methylene-11α,15α-bis-t-butyldimethylsilyloxy-16-o-chlorophenoxy-17,18,19,20-tetranorprosta-4,5,13-(trans)-trienoic acid methyl ester, (dl)-9-deoxy-9-methylene-11α,15α-bis-t-butyldimethylsilyloxy-16-m-chlorophenoxy-17,18,19,20-tetranorprosta-4,5,13-(trans)-trienoic acid methyl ester, (dl)-9-deoxy-9-methylene-11α,15α-bis-t-butyldimethylsilyloxy-16-p-chlorophenoxy-17,18,19,20-tetranorprosta-4,5,13-(trans)-trienoic acid methyl ester, (dl)-9-deoxy-9-methylene-11α,15α-bis-t-butyldimethylsilyloxy-16-o-bromophenoxy-17,18,19,20-tetranorprosta-4,5,13-(trans)-trienoic acid methyl ester, (dl)-9-deoxy-9-methylene-11α,15α-bis-t-butyldimethylsilyloxy-16-m-bromophenoxy-17,18,19,20-tetranorprosta-4,5,13-(trans)-trienoic acid methyl ester, (dl)-9-deoxy-9-methylene-11α,15α-bis-t-butyldimethylsilyloxy-16-p-bromophenoxy-17,18,19,20-tetranorprosta-4,5,13-(trans)-trienoic acid methyl ester, (dl)-9-deoxy-9-methylene-11α,15α-bis-t-butyldimethylsilyloxy-16-o-methylphenoxy-17,18,19,20-tetranorprosta-4,5,13-(trans)-trienoic acid methyl ester, (dl)-9-deoxy-9-methylene-11α,15α-bis-t-butyldimethylsilyloxy-16-m-methylphenoxy-17,18,19,20-tetranorprosta-4,5,13-(trans)-trienoic acid methyl ester, (dl)-9-deoxy-9-methylene-11α,15α-bis-t-butyldimethylsilyloxy-16-p-methylphenoxy-17,18,19,20-tetranorprosta-4,5,13-(trans)-trienoic acid methyl ester.

EXAMPLE 2

This example represents a method for converting compounds of Formula (3) to compounds of Formula (4).

50 mg of (dl)-9-deoxy-9-methylene-11α,15α-bis-t-butyldimethylsilyloxy-16-phenoxy-17,18,19,20-tetranorprosta-4,5,13-(trans)-trienoic acid methyl ester is dissolved in 20 ml tetrahydrofuran and 2 ml of 1 N lithium hydroxide is added with stirring. This solution is stirred at room temperature for 5 hours. The reaction mixture is then acidified to a pH of 4.5 with dilute acetic acid (1 M) and extracted with 4×25 ml ethyl acetate. Combined extracts are washed with saturated aqueous brine and the organic layer is dried with anhydrous sodium sulfate. The solution is then concentrated under vacuum and the concentrate chromatographed on silica gel thin-layer plates using ethyl acetate. The product is removed from the silica gel with ethyl acetate. Following filtration and flash evaporation of the solvent there is obtained ((dl)-9-deoxy-9-methylene-11α,15α-bis-t-butyldimethylsiloxy-16-phenoxy-17,18,19,20-tetranorprosta-4,5,13-(trans)-trienoic acid.

Similarily, substituting a stoichiometric equivalent amount of the methyl esters recited in Example 1 there are obtained:

(dl)-9-deoxy-9-methylene-11α,15α-bis-t-butyldimethylsilyloxy-16-o-fluorophenoxy-17,18,19,20-tetranorprosta-4,5,13-(trans)-trienoic acid, (dl)-9-deoxy-9-methylene-11α,15α-bis-t-butyldimethylsilyloxy-16-m-fluorophenoxy-17,18,19,20-tetranorprosta-4,5,13-(trans)-trienoic acid, (dl)-9-deoxy-9-methylene-11α,15α-bis-t-butyldimethylsilyloxy-16-p-fluorophenoxy-17,18,19,20-tetranorprosta-4,5,13-(trans)-trienoic acid, (dl)-9-deoxy-9-methylene-11α,15α-bis-t-butyldimethylsilyloxy-16-o-chlorophenoxy-17,18,19,20-tetranorprosta-4,5,13-(trans)-trienoic acid, (dl)-9-deoxy-9-methylene-11α,15α-bis-t-butyldimethylsilyloxy-16-m-chlorophenoxy-17,18,19,20-tetranorprosta-4,5,13-(trans)-trienoic acid, (dl)-9-deoxy-9-methylene-11α,15α-bis-t-butyldimethylsilyloxy-16-p-chlorophenoxy-17,18,19,20-tetranorprosta-4,5,13-(trans)-trienoic acid, (dl)-9-deoxy-9-methylene-11α,15α-bis-t-butyldimethylsilyloxy-16-o-bromophenoxy-17,18,19,20-tetranorprosta-4,5,13-(trans)-trienoic acid, (dl)-9-deoxy-9-methylene-11α,15α-bis-t-butyldimethylsilyloxy-16-m-bromophenoxy-17,18,19,20-tetranorprosta-4,5,13-(trans)-trienoic acid, (dl)-9-deoxy-9-methylene-11α,15α-bis-t-butyldimethylsilyloxy-16-p-bromophenoxy-17,18,19,20-tetranorprosta-4,5,13-(trans)-trienoic acid, (dl)-9-deoxy-9-methylene-11α,15α-bis-t-butyldimethylsilyloxy-16-o-methylphenoxy-17,18,19,20-tetranorprosta-4,5,13-(trans)-trienoic acid, (dl)-9-deoxy-9-methylene-11α,15α-bis-t-butyldimethylsilyloxy-16-m-methylphenoxy-17,18,19,20-tetranorprosta-4,5,13-(trans)-trienoic acid, (dl)-9-deoxy-9-methylene-11α,15α-bis-t-butyldimethylsilyloxy-16-p-methylphenoxy-17,18,19,20-tetranorprosta-4,5,13-(trans)-trienoic acid.

EXAMPLE 3

Compounds of Formula (4) may be converted to compounds of Formula (5) using the following method.

Lithium aluminum hydride, 5 mg, was added into 5 ml of diethyl ether. This solution was cooled under dry nitrogen to 10° C. and 230 mg of (dl)-9-deoxy-9-methylene-11α,15α-bis-t-butyldimethylsilyloxyl-16-phenoxy-17,18,19,20-tetranorprosta-4,5,13-(trans)-trienoic acid in 2 ml of ether added. After stirring for about 15 minutes, 1 ml of acetone was added after which 2 ml of a saturated potassium sodium tartrate solution. The resulting solution was extracted with ethyl acetate (5×5 ml). the combined organic layers were washed with a saturated brine solution (10 ml) and dried over sodium sulfate. Solvent was removed by flash evaporation and the residue chromatographed on silicia gel with 500 ml of ethyl acetate.

Substituting for the mentioned acid any of the compounds of Example (2) and following the procedure given above, there may be obtained the following alcohols:

(dl)-9-deoxy-9-methylene-11α,15α-bis-t-butyldimethylsilyloxy-16-o-fluorophenoxy-17,18,19,20-tetranorprosta-4,5,13-(trans)-trien-1-ol, (dl)-9-deoxy-9-methylene-11α,15α-bis-t-butyldimethylsilyloxy-16-m-fluorophenoxy-17,18,19,20-tetranorprosta-4,5,13-(trans)-trien-1-ol, (dl)-9-deoxy-9-methylene-11α,15α-bis-t-butyldimethylsilyloxy-16-p-fluorophenoxy-17,18,19,20-tetranorprosta-4,5,13-(trans)-trien-1-ol, (dl)-9-deoxy-9-methylene-11α,15α-bis-t-butyldimethylsilyloxy-16-o-chlorophenoxy-17,18,19,20-tetranorprosta-4,5,13-(trans)-trien-1-ol, (dl)-9-deoxy-9-methylene-11α,15α-bis-t-butyldimethylsilyloxy-16-m-chlorophenoxy-17,18,19,20-tetranorprosta-4,5,13-(trans)-trien-1-ol, (dl)-9-deoxy-9-methylene-11α,15α-bis-t-butyldimethylsilyloxy-16-p-chlorophenoxy-17,18,19,20-tetranorprosta-4,5,13-(trans)-trien-1-ol, (dl)-9-deoxy-9-methylene-11α,15α-bis-t-butyldimethylsilyloxy-16-o-bromophenoxy-17,18,19,20-tetranorprosta-4,5,13-(trans)-trien-1-ol, (dl)-9-deoxy-9-methylene-11α,15α-bis-t-butyldimethylsilyloxy-16-m-bromophenoxy-17,18,19,20-tetranorprosta-4,5,13-(trans)-trien-1-ol, (dl)-9-deoxy-9-methylene-11α,15α-bis-t-butyldimethylsilyloxy-16-p-bromophenoxy-17,18,19,20-tetranorprosta-4,5,13-(trans)-trien-1-ol, (dl)-9-deoxy-9-methylene-11α,15α-bis-t-butyldimethylsilyloxy-16-o-methylphenoxy-17,18,19,20-tetranorprosta-4,5,13-(trans)-trien-1-ol, (dl)-9-deoxy-9-methylene-11α,15α-bis-t-butyldimethylsilyloxy-16-m-methylphenoxy-17,18,19,20-tetranorprosta-4,5,13-(trans)-trien-1-ol, (dl)-9-deoxy-9-methylene-11α,15α-bis-t-butyldimethylsilyloxy-16-p-methylphenoxy-17,18,19,20-tetranorprosta-4,5,13-(trans)-trien-1-ol.

EXAMPLE 4

This example illustrates a method for converting compounds of Formula (5) to compounds of Formula (6).

0.77 g of anhydrous chromium trioxide is added to a stirred solution of 1.5 ml of dry pyridine in 20 ml of dry dichloromethane and stirred under a dry nitrogen atmosphere at 20° C. for 15 minutes after which a solution of 305 mg of (dl)-9-deoxy-9-methylene-11α,15α-bis-t-butyldimethylsilyloxy-16-phenoxy-17,18,19,20-tetranorprosta-4,5,13-(trans)-trien-1-ol in 10 ml of dry dichloromethane is added and the reaction mixture is stirred for 30 minutes at 20° C. The solution is decanted from the residue and the residue is washed with two 200 ml portions of diethyl ether. The organic solutions are combined, washed successively with two 350 ml portions of water and dried over anhydrous sodium sulphate. Evaporation under reduced pressure gives an oily residue which is chromatographed on a silica gel column, eluting with ethyl acetate-hexane (15:85), to yield (dl)-9-deoxy-9-methylene-11α,15α-bis-t-butyldimethylsilyloxy-16-phenoxy-17,18,19,20-tetranorprosta-4,5,13-(trans)-trien-1-aldehyde.

In like manner, substituting a stoichiometric equivalent amount of the trien-1-ol described in Example 3 there may be prepared the following compounds:

(dl)-9-deoxy-9-methylene-11α,15α-bis-t-butyldimethylsilyloxy-16-o-fluorophenoxy-17,18,19,20-tetranorprosta-4,5,13-(trans)-trien-1-aldehyde, (dl)-9-deoxy-9-methylene-11α,15α-bis-t-butyldimethylsilyloxy-16-m-fluorophenoxy-17,18,19,20-tetranorprosta-4,5,13-(trans)-trien-1-aldehyde, (dl)-9-deoxy-9-methylene-11α,15α-bis-t-butyldimethylsilyloxy-16-p-fluorophenoxy-17,18,19,20-tetranorprosta-4,5,13-(trans)-trien-1-aldehyde, (dl)-9-deoxy-9-methylene-11α,15α-bis-t-butyldimethylsilyloxy-16-o-chlorophenoxy-17,18,19,20-tetranorprosta-4,5,13-(trans)-trien-1-aldehyde, (dl)-9-deoxy-9-methylene-11α,15α-bis-t-butyldimethylsilyloxy-16-m-chlorophenoxy-17,18,19,20-tetranorprosta-4,5,13-(trans)-trien-1-aldehyde, (dl)-9-deoxy-9-methylene-11α,15α-bis-t-butyldimethylsilyloxy-16-p-chlorophenoxy-17,18,19,20-tetranorprosta-4,5,13-(trans)-trien-1-aldehyde, (dl)-9-deoxy-9-methylene-11α,15α-bis-t-butyldimethylsilyloxy-16-o-bromophenoxy-17,18,19,20-tetranorprosta-4,5,13-(trans)-trien-1-aldehyde, (dl)-9-deoxy-9-methylene-11α,15α-bis-t-butyldimethylsilyloxy-16-m-bromophenoxy-17,18,19,20-tetranorprosta-4,5,13-(trans)-trien-1-aldehyde, (dl)-9-deoxy-9-methylene-11α,15α-bis-t-butyldimethylsilyloxy-16-p-bromophenoxy-17,18,19,20-tetranorprosta-4,5,13-(trans)-trien-1-aldehyde, (dl)-9-deoxy-9-methylene-11α,15α-bis-t-butyldimethylsilyloxy-16-o-methylphenoxy-17,18,19,20-tetranorprosta-4,5,13-(trans)-trien-1-aldehyde, (dl)-9-deoxy-9-methylene-11α,15α-bis-t-butyldimethylsilyloxy-16-m-methylphenoxy-17,18,19,20-tetranorprosta-4,5,13-(trans)-trien-1-aldehyde, (dl)-9-deoxy-9-methylene-11α,15α-bis-t-butyldimethylsilyloxy-16-p-methylphenoxy-17,18,19,20-tetranorprosta-4,5,13-(trans)-trien-1-aldehyde.

EXAMPLE 5

The t-butyldimethylsilyloxy ether the compounds of Formulas (3), (4), (5) and (6) may be converted to their respective 11α,15α diols of Formulas (IA), (IB), (IC) and (ID) using the following method:

A solution of 146 mg of (dl)-9-deoxy-9-methylene-11α,15α-bis-t-butyldimethylsilyloxy-16-phenoxy-17,18,19,20-tetranorprosta-4,5,13-(trans)-trien-1-aldehyde in 1.4 ml of acetonitrile is added 0.1 ml of 48% hydrogen fluoride which is stirred at the room temperature for 1 hour.

Thereafter, the reaction solution is washed with aqueous sodium bicarbonate until neutral and the diol is extracted with ethyl acetate (5×10 ml). This extract is washed with 2×10 ml of saturated aqueous sodium chloride and dried over sodium sulfate. The oily residue is chromatographed on a silica gel column (10 g) with 30% ethyl acetate/hexane followed by 50% ethyl acetate/hexane. Combining appropriate fractions and removing the solvent under reduced pressure, there is obtained (dl)-9-deoxy-9-methylene-11α,15α-dihydroxy-16-phenoxy-17,18,19,20-tetranorprosta-4,5,13-(trans)-trien-1-aldehyde.

Proceeding in a like manner, but substituting for the mentioned aldehyde the methyl esters of Example 1, the acids of Example 2, the alcohols of Example 3 and the aldehydes of Example 4, there may be prepared the following 11α,15α diol containing compounds:

(dl)-9-deoxy-9-methylene-11α,15α-dihydroxy-16-o-fluorophenoxy-17,18,19,20-tetranorprosta-4,5,13-(trans)-trienoic acid methyl ester, (dl)-9-deoxy-9-methylene-11α,15α-dihydroxy-16-m-fluorophenoxy-17,18,19,20-tetranorprosta-4,5,13-(trans)-trienoic acid methyl ester, (dl)-9-deoxy-9-methylene-11α,15α-dihydroxy-16-p-fluorophenoxy-17,18,19,20-tetranorprosta-4,5,13-(trans)-trienoic acid methyl ester,
(dl)-9-deoxy-9-methylene-11α,15α-dihydroxy-16-o-chlorophenoxy-17,18,19,20-tetranorprosta-4,5,13-(trans)-trienoic acid methyl ester,
(dl)-9-deoxy-9-methylene-11α,15α-dihydroxy-16-m-chlorophenoxy-17,18,19,20-tetranorprosta-4,5,13-(trans)-trienoic acid methyl ester,
(dl)-9-deoxy-9-methylene-11α,15α-dihydroxy-16-p-chlorophenoxy-17,18,19,20-tetranorprosta-4,5,13-(trans)-trienoic acid methyl ester,
(dl)-9-deoxy-9-methylene-11α,15α-dihydroxy-16-o-bromophenoxy-17,18,19,20-tetranorprosta-4,5,13-(trans)-trienoic acid methyl ester,
(dl)-9-deoxy-9-methylene-11α,15α-dihydroxy-16-m-bromophenoxy-17,18,19,20-tetranorprosta-4,5,13-(trans)-trienoic acid methyl ester,
(dl)-9-deoxy-9-methylene-11α,15α-dihydroxy-16-p-bromophenoxy-17,18,19,20-tetranorprosta-4,5,13-(trans)-trienoic acid methyl ester,
(dl)-9-deoxy-9-methylene-11α,15α-dihydroxy-16-o-methylphenoxy-17,18,19,20-tetranorprosta-4,5,13-(trans)-trienoic acid methyl ester,
(dl)-9-deoxy-9-methylene-11α,15α-dihydroxy-16-m-methylphenoxy-17,18,19,20-tetranorprosta-4,5,13-(trans)-trienoic acid methyl ester,
(dl)-9-deoxy-9-methylene-11α,15α-dihydroxy-16-p-methylphenoxy-17,18,19,20-tetranorprosta-4,5,13-(trans)-trienoic acid methyl ether,
(dl)-9-deoxy-9-methylene-11α,15α-dihydroxy-16-o-fluorophenoxy-17,18,19,20-tetranorprosta-4,5,13-(trans)-trienoic acid,
(dl)-9-deoxy-9-methylene-11α,15α-dihydroxy-16-m-fluorophenoxy-17,18,19,20-tetranorprosta-4,5,13-(trans)-trienoic acid,
(dl)-9-deoxy-9-methylene-11α,15α-dihydroxy-16-p-fluorophenoxy-17,18,19,20-tetranorprosta-4,5,13-(trans)-trienoic acid,
(dl)-9-deoxy-9-methylene-11α,15α-dihydroxy-16-o-chlorophenoxy-17,18,19,20-tetranorprosta-4,5,13-(trans)-trienoic acid,
(dl)-9-deoxy-9-methylene-11α,15α-dihydroxy-16-m-chlorophenoxy-17,18,19,20-tetranorprosta-4,5,13-(trans)-trienoic acid,
(dl)-9-deoxy-9-methylene-11α,15α-dihydroxy-16-p-chlorophenoxy-17,18,19,20-tetranorprosta-4,5,13-(trans)-trienoic acid,
(dl)-9-deoxy-9-methylene-11α,15α-dihydroxy-16-o-bromophenoxy-17,18,19,20-tetranorprosta-4,5,13-(trans)-trienoic acid,
(dl)-9-deoxy-9-methylene-11α,15α-dihydroxy-16-m-bromophenoxy-17,18,19,20-tetranorprosta-4,5,13-(trans)-trienoic acid,
(dl)-9-deoxy-9-methylene-11α,15α-dihydroxy-16-p-bromophenoxy-17,18,19,20-tetranorprosta-4,5,13-(trans)-trienoic acid,
(dl)-9-deoxy-9-methylene-11α,15α-dihydroxy-16-o-methylphenoxy-17,18,19,20-tetranorprosta-4,5,13-(trans)-trienoic acid,
(dl)-9-deoxy-9-methylene-11α,15α-dihydroxy-16-m-methylphenoxy-17,18,19,20-tetranorprosta-4,5,13-(trans)-trienoic acid,
(dl)-9-deoxy-9-methylene-11α,15α-dihydroxy-16-p-methylphenoxy-17,18,19,20-tetranorprosta-4,5,13-(trans)-trienoic acid,
(dl)-9-deoxy-9-methylene-11α,15α-dihydroxy-16-o-fluorophenoxy-17,18,19,20-tetranorprosta-4,5,13-(trans)-trien-1-ol,
(dl)-9-deoxy-9-methylene-11α,15α-dihydroxy-16-m-fluorophenoxy-17,18,19,20-tetranorprosta-4,5,13-(trans)-trien-1-ol,
(dl)-9-deoxy-9-methylene-11α,15α-dihydroxy-16-p-fluorophenoxy-17,18,19,20-tetranorprosta-4,5,13-(trans)-trien-1-ol,
(dl)-9-deoxy-9-methylene-11α,15α-dihydroxy-16-o-chlorophenoxy-17,18,19,20-tetranorprosta-4,5,13-(trans)-trien-1-ol,
(dl)-9-deoxy-9-methylene-11α,15α-dihydroxy-16-m-chlorophenoxy-17,18,19,20-tetranorprosta-4,5,13-(trans)-trien-1-ol,
(dl)-9-deoxy-9-methylene-11α,15α-dihydroxy-16-p-chlorophenoxy-17,18,19,20-tetranorprosta-4,5,13-(trans)-trien-1-ol,
(dl)-9-deoxy-9-methylene-11α,15α-dihydroxy-16-o-bromophenoxy-17,18,19,20-tetranorprosta-4,5,13-(trans)-trien-1-ol,
(dl)-9-deoxy-9-methylene-11α,15α-dihydroxy-16-m-bromophenoxy-17,18,19,20-tetranorprosta-4,5,13-(trans)-trien-1-ol,
(dl)-9-deoxy-9-methylene-11α,15α-dihydroxy-16-p-bromophenoxy-17,18,19,20-tetranorprosta-4,5,13-(trans)-trien-1-ol,
(dl)-9-deoxy-9-methylene-11α,15α-dihydroxy-16-o-methylphenoxy-17,18,19,20-tetranorprosta-4,5,13-(trans)-trien-1-ol,
(dl)-9-deoxy-9-methylene-11α,15α-dihydroxy-16-m-methylphenoxy-17,18,19,20-tetranorprosta-4,5,13-(trans)-trien-1-ol,
(dl)-9-deoxy-9-methylene-11α,15α-dihydroxy-16-p-methylphenoxy-17,18,19,20-tetranorprosta-4,5,13-(trans)-trien-1-ol,
(dl)-9-deoxy-9-methylene-11α,15α-dihydroxy-16-o-fluorophenoxy-17,18,19,20-tetranorprosta-4,5,13-(trans)-trien-1-aldehyde,
(dl)-9-deoxy-9-methylene-11α,15α-dihydroxy-16-m-fluorophenoxy-17,18,19,20-tetranorprosta-4,5,13-(trans)-trien-1-aldehyde,
(dl)-9-deoxy-9-methylene-11α,15α-dihydroxy-16-p-fluorophenoxy-17,18,19,20-tetranorprosta-4,5,13-(trans)-trien-1-aldehyde,
(dl)-9-deoxy-9-methylene-11α,15α-dihydroxy-16-o-chlorophenoxy-17,18,19,20-tetranorprosta-4,5,13-(trans)-trien-1-aldehyde,
(dl)-9-deoxy-9-methylene-11α,15α-dihydroxy-16-m-chlorophenoxy-17,18,19,20-tetranorprosta-4,5,13-(trans)-trien-1-aldehyde,
(dl)-9-deoxy-9-methylene-11α,15α-dihydroxy-16-p-chlorophenoxy-17,18,19,20-tetranorprosta-4,5,13-(trans)-trien-1-aldehyde,
(dl)-9-deoxy-9-methylene-11α,15α-dihydroxy-16-o-bromophenoxy-17,18,19,20-tetranorprosta-4,5,13-(trans)-trien-1-aldehyde,
(dl)-9-deoxy-9-methylene-11α,15α-dihydroxy-16-m-bromophenoxy-17,18,19,20-tetranorprosta-4,5,13-(trans)-trien-1-aldehyde,
(dl)-9-deoxy-9-methylene-11α,15α-dihydroxy-16-p-bromophenoxy-17,18,19,20-tetranorprosta-4,5,13-(trans)-trien-1-aldehyde,
(dl)-9-deoxy-9-methylene-11α,15α-dihydroxy-16-o-methylphenoxy-17,18,19,20-tetranorprosta-4,5,13-(trans)-trien-1-aldehyde, (dl)-9-deoxy-9-methylene-11α,15α-dihydroxy-16-m-methylphenoxy-17,18,19,20-tetranorprosta-4,5,13-(trans)-trien-1-aldehyde, (dl)-9-deoxy-9-methylene-11α,15α-dihydroxy-16-p-methylphenoxy-17,18,19,20-tetranorprosta-4,5,13-(trans)-trien-1-aldehyde.

EXAMPLE 6

To a solution of 20 mg of (dl)-9-deoxy-9-methylene-11α,15α-dihydroxy-16-phenoxy-17,18,19,20-tetranoraprosta-4,5,13-(trans)-trienoic acid in 5 ml of methanol is added in mixture of 1 ml of concentrated ammonium hydroxide and 2 ml of methanol. The resulting mixture is stirred for two hours at room temperature and then evaporated to dryness to yield the ammonium salt of (dl)-9-deoxy-9-methylene-11α,15α-dihydroxy-16-phenoxy-17,18,19,20-tetranoraprosta-4,5,13-(trans)-trienoic acid.

By employing dimethylamine, diethylamine or dipropylamine in place of ammonium hydroxide in the above procedure, the corresponding salts of (dl)-9-deoxy-9-methylene-11α,15α-dihydroxy-16-phenoxy-17,18,19,20-tetranoraprosta-4,5,13-(trans)-trienoic acid are obtained. Following this procedure all the acids in Example 5 may be converted to the corresponding amine salt.

EXAMPLE 7

To a mixture of 30.6 mg of procaine (1.0 molar equivalent) and 1.5 ml of aqueous methanol is added, 50 mg of (dl)-9-deoxy-9-methylene-11α,15α-dihydroxy-16-phenoxy-17,18,19,20-tetranoraprosta-4,5,13-(trans)-trienoic acid and 10 ml of methanol and the resultant mixtures stirred at room temperature for 16 hours. It is then evaporated to dryness under reduced pressure to give the procaine salt of (dl)-9-deoxy-9-methylene-11α,15α-dihydroxy-16-phenoxy-17,18,19,20-tetranoraprosta-4,5,13-(trans)-trienoic acid.

Proceeding in a similiar manner, the lysine, caffeine, tromethamine and arginine salts are obtained.

EXAMPLE 8

This example illustrates a formulation preparation which may be used for preparing pharmaceutical compositions of compounds of the subject invention.

To 10 ml of anhydrous propylene carbonate at room temperature is added 5 mg of (dl)-9-deoxy-9-methylene-11α-15α-dihydroxy-16-phenoxy-17,18,19,20-tetranorprosta-4,5,13-(trans)-trienoic acid methyl ester. The mixture is stirred with a blade type stirrer for 15 minutes until a homogenous solution is obtained.

What is claimed is:

1. A compound selected from the group of those represented by the following Formula:

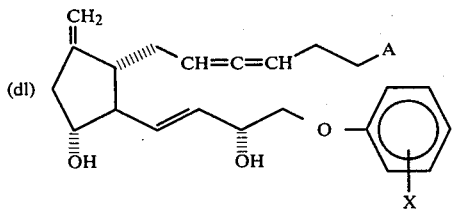

wherein A is CHOH, CHO or COOR wherein R is hydrogen, a lower alkyl group of 1 to 4 carbon atoms or the pharmaceutically acceptable, non-toxic salts of compounds in which R is hydrogen; and X is hydrogen, o-, m- or p-halo (fluoro, chloro or bromo), o-, m- or p-methyl or o-, m- or p-methoxy.

2. A compound according to claim 1 wherein A is COOR and X is hydrogen.

3. A compound according to claim 2 wherein R is hydrogen, (dl)-9-deoxy-9-methylene-11α,15α-dihydroxy-16-phenoxy-17,18,19,20-tetranorprosta-4,5,13-(trans)-trienoic acid.

4. A compound according to claim 2 wherein R is methyl, (dl)-9-deoxy-9-methylene-11α,15α-dihydroxy-16-phenoxy-17,18,19,20-tetranorprosta-4,5,13-(trans)-trienoic acid methyl ester.

5. A compound according to claim 2 wherein R is sodium, (dl)-9-deoxy-9-methylene-11α,15α-dihydroxy-16-phenoxy-17,18,19,20-tetranorprosta-4,5,13-(trans)-trienoic acid sodium salt.

6. A compound according to claim 2 wherein R is hydrogen and X is m-chloro, (dl)-9-deoxy-9-methylene-11α,15α-dihydroxy-16-m-chlorophenoxy-17,18,19,20-tetranorprosta-4,5,13-(trans)-trienoic acid.

7. A compound according to claim 2 wherein R is hydrogen and X is p-methyl, (dl)-9-deoxy-9-methylene-11α,15α-dihydroxy-16-p-methylphenoxy-17,18,19,20-tetranorprosta-4,5,13-(trans)-trienoic acid.

8. A compound according to claim 1 wherein R is hydrogen and X is m-methoxy, (dl)-9-deoxy-9-methylene-11α,15α-dihydroxy-16-m-methoxyphenoxy-17,18,19,20-tetranorprosta-4,5,13-(trans)-trienoic acid.

9. A compound according to claim 1 wherein A is CHOH.

10. A compound according to claim 9 wherein and X is hydrogen, (dl)-9-deoxy-9-methylene-11α,15α-dihydroxy-16-phenoxy-17,18,19,20-tetranorprosta-4,5,13-(trans)-trien-1-ol.

11. A compound according to claim 9 wherein X is o-chloro, (dl)-9-deoxy-9-methylene-11α,15α-dihyroxy-16-o-chlorophenoxy-17,18,19,20-tetranorprosta-4,5,13-(trans)-trien-1-ol.

12. A compound according to claim 9 wherein X is p-methyl, (dl)-9-deoxy-9-methylene-11α,15α-dihydroxy-16-p-methylphenoxy-17,18,19,20-tetranorprosta-4,5,13-(trans)-trien-1-ol.

13. A compound according to claim 9, wherein X is m-methoxy, (dl)-9-deoxy-9-methylene-11α,15α-dihydroxy-16-m-methoxyphenoxy-17,18,19,20-tetranorprosta-4,5,13-(trans)-trien-1-ol.

14. A compound according to claim 1 wherein A is CHO.

15. A compound according to claim 14 wherein X is hydrogen, (dl)-9-deoxy-9-methylene-11α,15α-dihydroxy-16-phenoxy-17,18,19,20-tetranorprosta-4,5,13-(trans)-trien-1-aldehyde.

16. A compound according to claim 14 wherein X is p-chloro, (dl)-9-deoxy-9-methylene-11α,15α-dihydroxy-16-p-chlorophenoxy-17,18,19,20-tetranorprosta-4,5,13-(trans)-trien-1-aldehyde.

17. A compound according to claim 14 wherein X is o-methyl, (dl)-9-deoxy-9-methylene-11α,15α-dihydroxy-16-o-methylphenoxy-17,18,19,20-tetranorprosta-4,5,13-(trans)-trien-1-aldehyde.

18. A pharmaceutical composition comprising a compound selected from the group represented by the

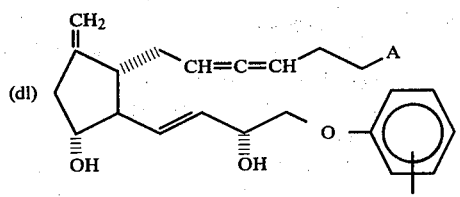

wherein A is CHOH, CHO or COOR wherein R is hydrogen, a lower alkyl group of 1 to 4 carbon atoms or the pharmaceutically acceptable, non-toxic salts of compounds in which R is hydrogen; and X is hydrogen, o, m- or p-halo (fluoro, chloro or bromo), o-, m- or p-methyl or o-, m- or p-methoxy; and a pharmaceutically acceptable excipient.

19. A process for preparing a compound of the formula

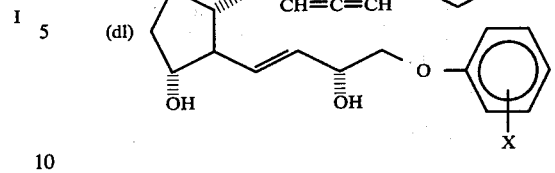

wherein A is CHOH, CHO or COOR; R is hydrogen or a lower alkyl group of 1 to 4 carbon atoms; and the pharmaceutically acceptable, non-toxic salts of compounds in which R is hydrogen; and X is hydrogen, o-, m- or p-halo (fluoro, chloro or bromo), o-, m- or p-methyl or o-, m- or p-methoxy which process comprises
  (a) reducing a compound of Formula I wherein A is COOR and R is hydrogen to a compound of Formula I wherein A is CHOH; or
  (b) oxidizing a compound of Formula I wherein A is CHOH to a compound of Formula I wherein A is CHO; or
  (c) converting a compound of Formula I wherein A is COOR and R is a lower alkyl group of 1 to 4 carbon atoms to a compound of Formula I wherein a is COOR and R is hydrogen by hydrolysis; or
  (d) converting a compound of Formula I wherein A is COOR and R is hydrogen to a compound of Formula I wherein R is a pharmaceutically acceptable, non-toxic salt.

* * * * *